United States Patent
McKay

(10) Patent No.: US 9,707,323 B2
(45) Date of Patent: Jul. 18, 2017

(54) DEVICES AND METHODS FOR INHIBITING ADHESION FORMATION

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 178 days.

(21) Appl. No.: 13/674,147

(22) Filed: Nov. 12, 2012

(65) Prior Publication Data

US 2014/0135285 A1   May 15, 2014

(51) Int. Cl.
*A61L 31/14* (2006.01)
*A61L 31/04* (2006.01)

(52) U.S. Cl.
CPC .......... *A61L 31/148* (2013.01); *A61L 31/044* (2013.01); *A61L 31/146* (2013.01); *A61L 2300/232* (2013.01)

(58) Field of Classification Search
CPC ... A61K 9/0002; A61K 9/0024; A61F 2/0063; A61L 27/58; A61L 27/24; A61L 31/148; A61L 31/044; A61L 31/146; A61L 2300/232
USPC ........ 623/11.11, 23.75, 23.72; 424/422–426, 424/444, 443, 451, 457, 484, 486, 488; 514/17.2, 59
See application file for complete search history.

(56) References Cited

U.S. PATENT DOCUMENTS

| | | | |
|---|---|---|---|
| 5,466,462 A * | 11/1995 | Rosenthal et al. | 424/426 |
| 5,605,938 A | 2/1997 | Roufa et al. | |
| 5,866,165 A | 2/1999 | Liu et al. | |
| 6,896,904 B2 | 5/2005 | Spiro et al. | |
| 6,905,105 B2 * | 6/2005 | Boyce | 249/112 |
| 2002/0045672 A1 * | 4/2002 | Harris | C08J 9/18 521/61 |
| 2002/0071855 A1 | 6/2002 | Sadozai et al. | |
| 2002/0090725 A1 * | 7/2002 | Simpson et al. | 435/402 |
| 2002/0151650 A1 | 10/2002 | Pathak et al. | |
| 2004/0037813 A1 * | 2/2004 | Simpson | A61F 2/08 424/93.7 |
| 2004/0193088 A1 | 9/2004 | Looney et al. | |
| 2005/0008620 A1 * | 1/2005 | Shimp | A61L 27/3608 424/93.7 |
| 2006/0247791 A1 * | 11/2006 | McKay et al. | 623/23.51 |
| 2007/0031498 A1 * | 2/2007 | Zong et al. | 424/486 |

(Continued)

FOREIGN PATENT DOCUMENTS

WO    2004105737 A2    12/2004

OTHER PUBLICATIONS

Klak et al. Mastered Proteolysis of Gelatin Gel Can Control Delivery Kinetics of Entrapped Large Molecules. Soft Matter, the Royal Society of Chemistry. 2012 (8): 4750-4755.*

*Primary Examiner* — Christopher D. Prone
*Assistant Examiner* — Rokhaya Diop

(57) ABSTRACT

Methods and compositions are provided for reducing, treating or preventing adhesions in a patient in need of such treatment. In one embodiment, an implantable device is provided for reducing or preventing adhesion formation at a post-operative tissue site in a patient, the implantable device including a biodegradable porous matrix comprising dextran, wherein the implantable device is capable of releasing the dextran over at least 2 days.

15 Claims, 2 Drawing Sheets

(56) References Cited

U.S. PATENT DOCUMENTS

2007/0191963 A1\* 8/2007 Winterbottom et al. .... 623/23.5
2011/0002999 A1 1/2011 Chen et al.
2011/0274742 A1 11/2011 Arinzeh et al.

\* cited by examiner

DEVICES AND METHODS FOR INHIBITING ADHESION FORMATION

BACKGROUND

Surgical adhesions are abnormal fibrous bands of scar tissue that can form inside the body as a result of the healing process that often follows open or minimally invasive surgical procedure including abdominal, gynecologic, cardiothoracic, spinal, plastic, vascular, ENT, ophthalmologic, urologic, neuro, or orthopedic surgery.

Surgical adhesions are typically connective tissue structures that form between adjacent injured areas within the body. Briefly, localized areas of injury trigger an inflammatory and healing response (clotting) that culminates in healing and scar tissue formation. If scarring results in the formation of fibrous tissue bands or adherence of adjacent anatomical structures (that should normally be separate), adhesion formation is said to have occurred.

Adhesions can range from flimsy, easily separable structures to dense, tenacious fibrous structures that can only be separated by surgical dissection. While many adhesions are benign, many adhesions can cause major pain. For example, adhesions to nerve structures (i.e. nerve root, spinal cord) and other vital structures after spinal surgery result in post-operative pain and make revision surgery difficult and potentially dangerous if necessary. More specifically, after spinal surgery if adhesions form they may cause tethering of spinal nerve roots and dorsal root ganglia, which often causes recurrent radicular pain that can be very debilitating to the patient and often leads to repeated surgical intervention.

Since most surgery involves a certain degree of trauma to the operative tissues, virtually any procedure (no matter how well executed) has the potential to result in the formation of clinically significant adhesion formation. Adhesions can be triggered by surgical trauma such as cutting, manipulation, retraction or suturing, as well as from inflammation, infection (e.g., fungal or mycobacterium), bleeding or the presence of a foreign body. Surgical trauma may also result from tissue drying, ischemia, or thermal injury. Due to the diverse etiology of surgical adhesions, the potential for formation exists regardless of whether the surgery is done in a so-called minimally invasive fashion (e.g., catheter-based therapies, laparoscopy) or in a standard open technique involving one or more relatively large incisions. Although a potential complication of any surgical intervention, surgical adhesions are particularly problematic in GI surgery (causing bowel obstruction), gynecological surgery (causing pain and/or infertility), tendon repairs (causing shortening and flexion deformities), joint capsule procedures (causing capsular contractures), and nerve and muscle repair procedures (causing diminished or lost function).

Surgical adhesions may cause various, often serious and unpredictable clinical complications; some of which manifest themselves only years after the original procedure was completed. Complications from surgical adhesions are a major cause of failed surgical therapy and are the leading cause of bowel obstruction and infertility. Other adhesion-related complications include chronic back or pelvic pain, intestinal obstruction, urethral obstruction and voiding dysfunction.

Relieving the post-surgical complications caused by adhesions generally requires another surgery. However, the subsequent surgery is further complicated by adhesions formed as a result of the previous surgery. In addition, the second surgery is likely to result in further adhesions and a continuing cycle of additional surgical complications.

Thus, there is a need to reduce, prevent, or treat adhesions. New devices, compositions and methods that reliably prevent in-growth of scar tissue and formation or reformation of adhesions at or near the target tissue site while an injured tissue heals are needed.

SUMMARY

New devices, compositions and methods are provided that effectively reduce, prevent or treat adhesions. In some embodiments, the present disclosure provides implantable devices comprising biodegradable matrices for preventing adhesion formation, methods of making the matrices and methods of using these matrices.

In some embodiments, there is an implantable device for reducing or preventing adhesion formation at a post-operative tissue site in a patient, the implantable device comprising a biodegradable porous matrix including dextran, wherein the implantable device is configured to release the dextran over a period of at least 2 days.

In some embodiments, there is an implantable device for reducing or preventing adhesion formation at a post-operative tissue site in a patient, the implantable device comprising a biodegradable porous matrix comprising dextran sulfate, wherein the implantable device is configured for releasing the dextran sulfate over a period of at least 7 days.

In some embodiments, there is a method of reducing, preventing or treating adhesions in a patient in need of such treatment, the method comprising administering a biodegradable matrix comprising a therapeutically effective amount of dextran at or near a target tissue site beneath the skin of the patient, wherein the biodegradable matrix is configured to release an effective amount of the dextran over a period of at least 2 days.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
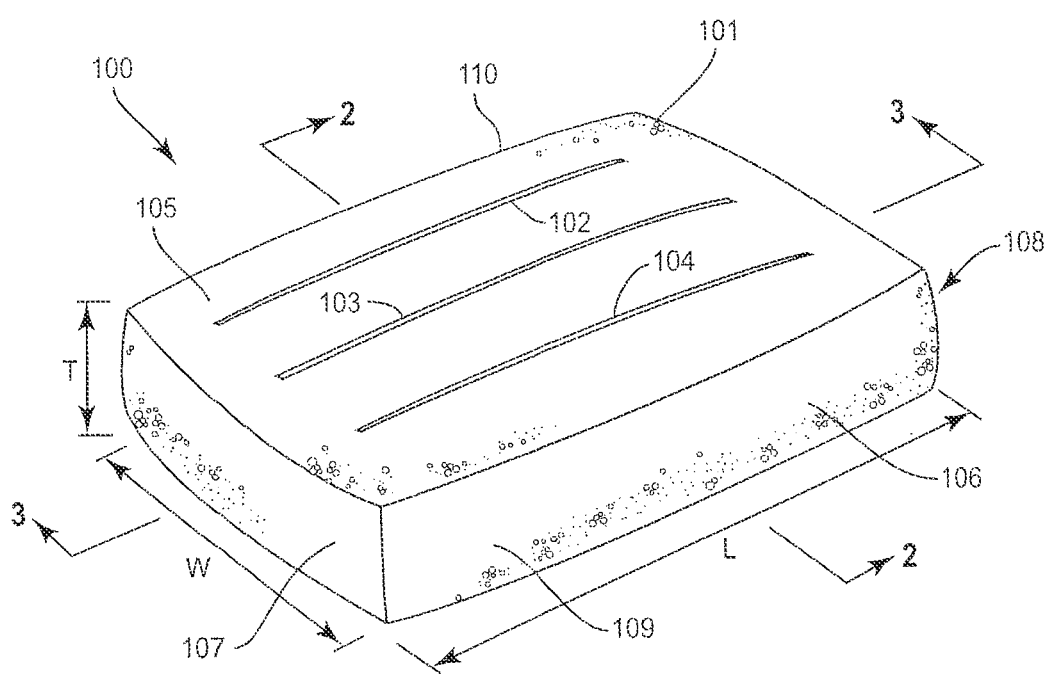
FIG. 1 depicts a perspective view of an exemplary matrix comprising an implant body defining a plurality of score lines according to an aspect of the present application.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "a matrix" includes one, two, three or more drug matrices.

A "drug depot" is the device in which the dextran sulfate composition is administered to the body. In some embodiments, the drug depot can be a matrix. Thus, a drug depot may comprise a physical structure to facilitate implantation and retention in a desired site (e.g., a disc space, a spinal canal, a tissue of the patient, particularly at or near a site of chronic pain, etc.). The drug depot may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.01 cm to about 20 cm from the administration site and comprises dextran. A drug depot includes a matrix, a pump, an implant body or pellet.

A "therapeutically effective amount" or "effective amount" is such that when administered, the drug results in alteration of the biological activity, such as, for example, inhibition of inflammation, reduction or alleviation of pain or adhesions, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the matrix will degrade over time by the action of enzymes, by hydrolytic action and/or by other similar mechanisms in the human body. In various embodiments, "biodegradable" includes that the depot (e.g., matrix, etc.) can break down or degrade within the body to non-toxic components after or while a therapeutic agent has been or is being released. By "bioerodible" it is meant that the depot (e.g., matrix, etc.) will erode or degrade over time due, at least in part, to contact with substances found in the surrounding tissue, fluids or by cellular action. By "bioabsorbable" it is meant that the depot (e.g., matrix, etc.) will be broken down and absorbed within the human body, for example, by a cell or tissue. "Biocompatible" means that the depot (e.g., matrix, etc.) will not cause substantial tissue irritation or necrosis at the target tissue site.

In some embodiments, the matrix has pores that allow release of the drug from the depot. The matrix will allow fluid in the depot to displace the drug. However, cell infiltration into the depot will be prevented by the size of the pores of the depot. In this way, in some embodiments, the depot should not function as a tissue scaffold and allow tissue growth. Rather, the matrix will solely be utilized for drug delivery. In some embodiments, the pores in the matrix will be less than 250 to 500 microns. This pore size will prevent cells from infiltrating the matrix and laying down scaffolding cells. Thus, in this embodiment, drug will elute from the matrix as fluid enters the matrix, but cells will be prevented from entering. In some embodiments, where there are little or no pores, the drug will elute out from the matrix by the action of enzymes, by hydrolytic action and/or by other similar mechanisms in the human body. In some embodiments, the matrix has pores that are greater than 250 to 500 microns to allow certain type of cell to infiltrate the matrix and lay down scaffolding cells.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The two types of formulations (sustained release and immediate release) may be used in conjunction. The sustained release and immediate release may be in one or more of the same depots (e.g., matrices). In various embodiments, the sustained release and immediate release may be part of separate depots. For example a bolus or immediate release formulation of a dextran sulfate composition may be placed at or near the target site and a sustain release formulation may also be placed at or near the same site. Thus, even after the bolus becomes completely accessible, the sustain release formulation would continue to provide the active ingredient for the intended tissue.

In various embodiments, the matrix can be designed to cause an initial burst dose of therapeutic agent within the first twenty-four to seventy-two hours after implantation. "Initial burst" or "burst effect" or "bolus dose" refers to the release of therapeutic agent from the depot during the first twenty-four hours to seventy-two hours after the depot comes in contact with an aqueous fluid (e.g., synovial fluid, cerebral spinal fluid, etc.). The "burst effect" is believed to be due to the increased release of therapeutic agent from the depot. In alternative embodiments, the depot (e.g., gel) is designed to avoid or reduce this initial burst effect (e.g., by applying an outer polymer coating to the depot). In some embodiments, the matrix has a burst release surface that releases about 10%, 15%, 20%, 25%, 30%, 35%, 45%, to about 50% of the drug over 24 or 48 hours.

"Treating" or "treatment" of a disease or condition refers to executing a protocol that may include administering one or more drugs to a patient (human, other normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition. In addition, treating or treatment does not require complete alleviation of signs or symptoms, does not require a cure, and specifically includes protocols that have only a marginal effect on the patient. "Reducing pain and/or inflammation and/or adhesion formation" includes a decrease in pain and/or inflammation and/or adhesion formation and does not require complete alleviation of pain and/or inflammation and/or adhesion signs or symptoms, and does not require a cure. In various embodiments, reducing inflammation and/or adhesion formation includes even a marginal decrease in inflammation and/or adhesion formation. By way of example, the administration of the effective dosage of a dextran sulfate composition may be used to prevent, treat or relieve the symptoms of inflammation and/or adhesion formation for different conditions. These conditions may comprise post-operative surgical sites.

The term "implantable" as utilized herein refers to a biocompatible device (e.g., drug depot (e.g., matrices) retaining potential for successful placement within a mammal. The expression "implantable device" and expressions of the like import as utilized herein refers to an object implantable through surgery, injection, or other suitable means whose primary function is achieved either through its physical presence or mechanical properties.

Dextran

According to some embodiments, a device is provided for reducing and/or eliminating adhesion formation after surgery is performed. In some embodiments, this device involves the incorporation of a composition for inhibiting cell migration such as dextran into a porous biodegradable matrix such as a sponge or capsule. Use of this device includes placing the device at the tissue site to be protected from scar formation, such as over a nerve structure or other vital structures, after the necessary surgery has been performed.

Advantageously, the device provides slow release of the cell migration inhibitor composition (dextran) over the healing period. The length of the composition's release can be regulated or adjusted by, e.g., the degree or amount of cross-linking of the matrix material. The presence of, e.g., dextran and its slow release over time acts to inhibit migration of cells such as fibroblasts into the surgical site, therefore reducing adhesions and scar formation.

In various embodiments, device(s), e.g., biodegradable device(s) incorporating dextran and methods are provided that have anti-adhesion effects in a single matrix or multiple matrices. New dextran compositions and methods are provided, which can easily allow accurate and precise implantation of a matrix containing the dextran with minimal physical and psychological trauma to a patient. One advantage of the dextran compositions and methods is that the drug depot (e.g., matrices) can now be easily delivered to the target tissue site (e.g., abdomen, synovial joint, at or near the spinal column, etc.) and reduce, prevent or treat adhesion formation. In this way, accurate and precise implantation of the matrix in a minimally invasive procedure can be accomplished.

In some embodiments, the device comprises a drug depot (e.g., matrix) including a dextran is incorporated in the matrix in an amount of from about 5 wt. % to about 70 wt. % and preferably about 10 wt. % to about 50 wt. % based on the weight of the matrix and the matrix can be used to improve prevent adhesion formation by, among other things, inhibiting cell migration.

Dextran is a complex, branched glucan (polysaccharide made of many glucose molecules) composed of chains of varying lengths (from 3 to 2000 kilodaltons). It is used medicinally as an antithrombotic (anti-platelet), to reduce blood viscosity, and as a volume expander in anemia. The antithrombotic effect of dextran is mediated through its binding of erythrocytes, platelets, and vascular endothelium, increasing their electronegativity and thus reducing erythrocyte aggregation and platelet adhesiveness.

Dextran used in the matrix of the current disclosure can have a wide range of average molecular weights from about 1,000 Daltons to about 1,000,000 Daltons e.g., about 10,000 Daltons to about 500,000 Daltons. In some embodiments, the dextran can have an average molecular weight of about 1.5 million to about 2.5 million Daltons.

In some embodiments, the dextran used in the matrix may have a low molecular weight dextran, e.g. 10 from a few hundred or thousand Daltons to high molecular weight dextran, generally with a molecular weight over 500,000 Daltons, e.g. >1,000,000 Daltons. In some embodiments, the Dextran can have an average molecular weight of about 500,000 to about 1,000,000 and more particularly about 500,000 to about 750,000 Daltons. In some embodiments, the dextran can have an average molecular weight of about 3,000 to about 250,000 Daltons, about 5,000 to about 100,000 Daltons, and about 10,000 to about 60,000 Daltons.

In some embodiments, the dextran comprises dextran sulfate. In some embodiments, the sulfur content of the dextran can be increased, e.g., the number of sulfate groups per glucosyl residue in the dextran chain. The average sulfur content for dextran may be about 10 to 25%, such as 16 to 19%, corresponding to about two sulfate groups per glucosyl residue. For dextran sulfate with an average molecular weight higher than 20,000 Daltons, a larger sulfur content could be employed.

The amounts of dextran in the matrix will depend on the severity of the condition, and on the patient to be treated, as well as the matrix used and administration route employed. The concentration of the dextran used should not be too high in order to minimize any side-effects associated with dextran. In clinical situations suitable doses of dextran in humans are those that give a mean blood concentration below 20 mg/ml, probably less than 15 mg/ml and especially less than 10 mg/ml. A preferred concentration range is between 20 mg/ml and 1 mg/ml dextran, such as more than 2 mg/ml, more than 4 mg/ml, more than 6 mg/ml, more than 8 mg/ml, or more than 10 and/or less than 20 mg/ml, less than 18 mg/ml, less than 16 mg/ml, less than 14 mg/ml, or less than 12 mg/ml, e.g. within the concentration range of 20 mg/ml and 1 mg/ml and/or 10 mg/ml and 2 mg/ml. The above-identified dosages are examples of preferred dosages of the average case. However, there can be individual instances where higher or lower dosage ranges are merited, and such are within the scope of the invention.

In some embodiments, the matrix can comprise dextran uniformly disposed throughout it. In some embodiments, the dextran can be disposed at discrete regions of the matrix. In some embodiments, the matrix can comprise fibers having the dextran disposed within the fibers (e.g., electrospun dextran fibers). The fibers may, in some embodiments, have a diameter ranging from 0.75 microns to 1.25 microns.

The amount of dextran per matrix can vary widely, depending on the size of device that is being manufactured, with typical device formulations using from about 0.001-0.2 g of dextran per device. However, the range can be extended widely, e.g. from as low as about 0.0001 g or less (for small devices) to as high as 1 or more g per device, for large devices. In some embodiments, it may be helpful to use lesser amounts of dextran (e.g. about 0.00001 to about 0.0001 g of dextran per device) in order to concentrate the active agents that are delivered by the device into a smaller volume. In some embodiments, the matrix comprises from about 5 wt. % to about 70 wt. % preferably about 10 wt. % to about 50 wt. % dextran based on the total weight % of the implantable device.

In some embodiments, the dextran can be in polymer form that have acetate, propionate, and/or succinate groups attached via ester linkages to a significant fraction of the dextran polymer's hydroxyl groups. In one embodiment, the dextran polymer comprises dextran acetate, dextran propionate, dextran succinate, dextran acetate propionate, dextran acetate succinate, dextran propionate succinate, dextran acetate propionate succinate, dextran sulfate, or mixtures thereof. In another embodiment, the dextran polymer comprises dextran acetate succinate, dextran propionate succinate, dextran acetate propionate succinate, dextran sulfate or mixtures thereof. In another embodiment, the dextran polymer comprises dextran acetate succinate. In yet another embodiment, the dextran polymer comprises dextran propionate succinate.

In some embodiments, the dextran can be an aminated dextran that can have an average molecular weight of about 1,000 to about 1,000,000 Daltons, more particularly about 500,000 to about 1,000,000 Daltons, and more particularly about 500,000 to about 750,000 Daltons. In some embodiments, the aminated dextran can have an average molecular weight of about 3,000 to about 250,000 Daltons, about 5,000 to about 100,000 Daltons, and about 10,000 to about 60,000 Daltons, and an amine substitution level of about 1% to about 65%, more particularly about 1% to about 40%, more particularly about 1% to about 5%, and more particularly about 2% to about 3%.

Other compounds other than dextran sulfate that have the property of inhibiting cell migration may be used in addition to, or instead of, dextran sulfate.

Generally, a matrix according to the present disclosure may comprise a single or multi-compartment structure capable of at least partially retaining a substance, such as a cell migration inhibitor composition provided therein, until the structure is placed at a surgical site. In some examples, upon placement, the matrix may facilitate transfer of the substance and/or materials surrounding the surgical site. The matrix may participate in, control, or otherwise adjust, the release of the substance and/or penetration of the matrix by surrounding materials, such as cells or tissues. Alternately, the matrix may include at least an impenetrable portion for preventing release of the substance and/or penetration of the matrix by surrounding materials.

A matrix according to an aspect of the present disclosure may comprise one or more bioerodible polymers, bioabsorbable polymers, biodegradable biopolymers, synthetic polymers, copolymers and copolymer blends or combinations thereof. Exemplary materials may include biopolymers and synthetic polymers such as human skin, human hair, bone sheets, collagen, fat, thin cross-linked sheets containing fibers and/or fibers and chips, degradable sheets made from polyethylene glycol (PEG), chitosan sheets, alginate sheets, cellulose sheets, hyaluronic acid sheet, as well as copolymer blends of poly (lactide-co-glycolide) PLGA.

Advantageously, in some embodiments, a matrix comprising a sponge configuration allows for the adhesion prevention device to occupy a larger volumetric space (than a thin sheet) adjacent to the nerve structure being protected. Further, the sponge will also absorb body fluids at the surgical site and will better stay in place at the nerve or vital structure.

In some embodiments, some amount of the cell inhibitor composition (such as dextran sulfate) will be released upon implantation of the matrix, but the matrix will also enable gradual, slow release of the cell inhibitor composition as the matrix resorbs over time. For example, in the case of a collagen matrix, the length of time release may be dependent on the degree of collagen crosslinking performed.

According to one embodiment, an implantable device is provided comprising a biodegradable matrix into which is incorporated dextran in an amount from about 5 wt. % to about 70 wt. %, preferably about 10 wt. % to about 50 wt. % of the implantable device. In some embodiments, the implantable device is capable of releasing the therapeutically effective dosage amount for 2-90 days, 2-10 days, 2-14 days, 2-21 days, 2-30 days; 2-90 days, 3-7 days, 3-10 days, 3-14 days, 3-21 days, 3-30 days, 3-60 days, 3-90 days or longer.

In some embodiments, the matrix can be designed to release (i) a bolus dose of the therapeutic composition (e.g., dextran) at a site beneath the skin; and (ii) an effective amount of the composition over a period of at least seven days.

Cell migration into the matrix and surgical area will be minimized due to the presence of cell inhibitor composition (such as dextran sulfate) on the matrix and its slow release over time. Further, the lower dose of cell inhibitor composition which is released gradually over time will provide an environment in which desired adjacent tissue repair can proceed and occur unaffected.

Matrix

The implantable device may for example, be a matrix that is part of a drug depot. The matrix (e.g., drug depot) may: (i) consist of the cell migration inhibitor composition (e.g., dextran) and the biodegradable device(s); (ii) consist essentially of the cell migration inhibitor composition and the biodegradable device(s); or (iii) comprise the cell migration inhibitor composition and the biodegradable device(s) and one or more other active ingredients, surfactants, excipients or other ingredients or combinations thereof. When there are other active ingredients, surfactants, excipients or other ingredients or combinations thereof in the formulation, in some embodiments these other compounds or combinations thereof comprise less than 50 wt. %, less than 40 wt. %, less than 30 wt. %, less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %.

In some embodiments, the matrix may comprise polyethylene glycol having an average molecular weight of from about 1,000 to about 10,000 and be in the matrix in an amount of from about 10 wt. % to about 60 wt. % and is released there from for additional tissue protection.

The matrix provides a scaffold to release a cell migration inhibitor composition in vivo in three dimensions. The matrix provides a more consistent and larger volume of scar free space around critical tissues than prior anti-adhesion devices. In some embodiments, one or more tissue matrices are stacked on one another at or near the target tissue site to aid in reducing or inhibiting adhesion formation.

A matrix of the present disclosure may be formulated in several physical forms, including sponge-like forms. Several alternate designs are possible including use of various biomaterial carriers (other than collagen) and forms and shapes.

In some embodiments, the matrix comprises a plurality of pores. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, the matrix has a porosity of at least about 30%, at least about 50%, at least about 60%, at least about 70%, at least about 90%. The pores enhance release of the dextran sulfate composition and may support ingrowth of cells, formation or remodeling of bone, cartilage and/or vascular tissue after release of most of the dextran sulfate or similar acting compound.

In some embodiments, the matrix may comprise natural and/or synthetic material. For example, the tissue scaffold may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, PEAs, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, caprolactone, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyrrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In some embodiments, the matrix comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type) (XVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the matrix comprises collagen-containing biomaterials from the implant market which, when placed in a bone defect, provide scaffolding around which the patient's new bone will grow, gradually replacing the carrier matrix as the target site heals. Examples of suitable carrier matrices may include, but are not limited to, bone matrix, e.g., the MasterGraft® Matrix produced by Medtronic Sofamor Danek, Inc., Memphis, Tenn.; putty, e.g., MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. Healos® marketed by Johnson & Johnson, USA; collagen sponges, e.g. Hemostagene® marketed by Coletica S A, France, or e.g. Helisat® marketed by Integra Life Sciences Inc., USA; and bone graft matrix, e.g., Collagraft® produced by Zimmer Holdings, Inc., Warsaw, Ind.

In some embodiments, the matrix has a thickness of from 0.25 mm to 5 mm, or from about 0.4 mm to about 2 mm, or 0.4 mm to about 1 mm. Clearly, different surgical sites (e.g., laminectomy, discectomy, facetectomy) may require different matrix thicknesses.

In some embodiments, the matrix has a density of between about 1.6 g/cm$^3$, and about 0.05 g/cm$^3$. In some embodiments, the matrix has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

The shape of the matrix may be tailored to the site at which it is to be situated. For example, it may be in the shape of a morsel, a plug, a pin, a peg, a cylinder, a block, a wedge, a sheet, etc. In some embodiments, the matrix comprises a thicker section in the middle where a larger tissue void space is desired. In one embodiment, the matrix is H shaped and is configured to fit into a spinal laminectomy site. In one embodiment, the matrix can be cut, broken and/or ripped into a particular dimension so as to conform to the area of the site.

In some embodiments, the diameter or diagonal of the matrix can range from 1 mm to 50 mm. In some embodiments, the diameter or diagonal of the matrix can range from 1 mm to 30 mm, or 5 mm to 10 mm which is small enough to fit through an endoscopic cannula, but large enough to minimize the number of matrices needed to fill a large tissue defect (e.g., defect at or near a nerve).

In some embodiments, the matrix containing dextran of the current application, prevents adhesions and scar tissue formation more consistently in a larger volume or space around vital structures such as nerve tissue. In some embodiments, the matrix comprises a three-dimensional sponge shape and cohesive matrix prevents tissue growth more than prior art flowable gel and thin membrane products.

In some embodiments, one or more surfaces of the matrix comprise a barrier that can be made by cross-linking the matrix to prevent unwanted tissue growth. In addition, the dextran can act synergistically to prevent adhesion of scar tissue formation at or near the target tissue site where the matrix is placed. In some embodiments, the dextran is uniformly distributed throughout the matrix at a concentration of about 2-10% mg/ml concentration. In some embodiments, the dextran can be at discrete positions in or on a surface of the matrix. In some embodiments, the dextran can be disposed in the barrier portion of the matrix. In some embodiments, the dextran is disposed only in the non-barrier portion of the matrix.

The dextran, in some embodiments, can be in the matrix in the matrix at a concentration of about 0.5 to about 25% mg/ml as shown in the table below. All the ranges in the table should be considered in "about" the range indicated. The dextran (DS) concentration in % solid concentration of dextran in the w/v can be from about 5% to about % 83% w/v or w/w or v/v. The concentration of collagen in the matrix can be from about 0.5% to about 1% w/v.

In some embodiments, the matrix may be made by injection molding, compression molding, blow molding, thermoforming, die pressing, slip casting, electrochemical machining, laser cutting, water jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

In some embodiments, a therapeutic agent (including one or more dextran compositions) may be disposed on or in the matrix by hand by soaking, electrospraying, ionization spraying or impregnating, vibratory dispersion (including sonication), nozzle spraying, compressed-air-assisted spraying, brushing and/or pouring.

Drugs, growth factors, polypeptides, proteins, cDNA, gene constructs and other therapeutic agents may also be included in the matrix and can be entrapped within the sponge either by mixing the agent with one of the two derivatives before gelatinization, or diffusion from a drug solution into the sponge after their formation. The therapeutic agent may also be covalently linked to the matrix.

The matrix may be formulated into a sponge-like material that is desirable for an implantable formulation. The matrices of the present disclosure may be formed into any shape by lyophilization or air drying in molds of the desired shape.

Growth factors and/or therapeutic agents may be included in the matrix, and can include proteins originating from various animals including humans, microorganisms and plants, as well as those produced by chemical synthesis and using genetic engineering techniques. Such agents include, but are not limited to, biologically active substances such as growth factors such as, bFGF, aFGF, EGF (epidermal growth factor), PDGF (platelet-derived growth factor), IGF (insulin-like growth factor), TGF-.beta. 1 through 3, including the TGF-beta superfamily (BMPs, GDF-5, ADMP-1 and dpp); cytokines, such as various interferons, including interferon-alpha, -beta and -gamma, and interleukin-2 and -3; hormones, such as, insulin, growth hormone-releasing factor and calcitonin; non-peptide hormones; antibiotics; anti-cancer agents and chemical agents, such as, chemical mimetics of growth factors or growth factor receptors, and gene and DNA constructs, including cDNA constructs and genomic constructs. In a preferred embodiment, the agents include those factors, proteinaceous or otherwise, which are found to play a role in the induction or conduction of growth of bone, ligaments, cartilage or other tissues associated with bone or joints, such as for example, BMP and bFGF. The present disclosure also encompasses the use of autologous or allogeneic cells encapsulated within the matrix. The autologous cells may be those naturally occurring in the donor or cells that have been recombinantly modified to contain nucleic acid encoding desired protein products.

As will be understood by those of skill in the art, the amount of agent to be immobilized or encapsulated within

| | | Dextran Concentration | | | | | | |
|---|---|---|---|---|---|---|---|---|
| | | [mg/mL] | 0.5 | 2.5 | 5 | 10 | 15 | 20 | 25 |
| | | [w/v] | 0.05% | 0.25% | 0.5% | 1.0% | 1.5% | 2.0% | 2.5% |
| Collagen | 0.5% | % DS in | 9% | 33% | 50% | 67% | 75% | 80% | 83% |
| Conc. [w/v %] | 1% | Solid | 5% | 20% | 33% | 50% | 60% | 67% | 71% | the carrier will vary depending upon the intended target, but will usually be in the range of pictogram, nanogram, milligram, to gram quantities.

A matrix of the present disclosure may be administered through implantation or direct application depending on the intended application. In some embodiments, the matrix may comprise sterile and/or preservative free material. The matrix can be implanted by hand or machine in procedures such as for example, laparoscopic, arthroscopic, neuroendoscopic, endoscopic, rectoscopic procedures or the like.

In some embodiments, the matrix may be in the form of a porous collagen sponge that can be spray coated, embedded or imparted with a cell migration inhibitor composition such as dextran sulfate, and as the sponge degrades, the composition may be gradually released over time.

As shown in FIG. 1, the medical device, in this embodiment, may be in matrix form 101 comprising an implant body 100 including a surface that may provide an initial burst release of the cell migration inhibitor composition. Therefore, on implantation, the matrix will immediately release the cell migration inhibitor composition (e.g., dextran) to provide its therapeutic effect locally at the target tissue site. This is particularly beneficial to reduce adhesion formation at the tissue site.

In some embodiments, the initial burst surfaces can be disposed on the edges of the matrix so that upon contact with the target tissue site, the edges will begin to release the cell migration inhibitor composition. In some embodiments, the core of the matrix can comprise dense, entangled polymers and have the cell migration inhibitor composition (e.g., dextran) to provide slower release of the cell migration inhibitor composition.

Alternatively, the cell migration inhibitor composition (e.g., dextran) can be disposed homogenously throughout the matrix to provide continuous extended release of the cell migration inhibitor composition. In some embodiments, the cell migration inhibitor composition can be layered in the matrix with some portions having different concentrations to provide burst release and then slower release of the cell migration inhibitor composition in areas that have dense crosslinked polymers, such as for example, in the core of the matrix.

While FIG. 1 depicts a matrix 101 in a rectangular form, alternate shapes and configurations may be contemplated. In further exemplary embodiments, the matrix may be a narrow tube for delivery through a catheter. For example, the matrix may be delivered percutaneously using a catheter through which it is inserted. Thus, the matrix may have dimensions suitable for receipt in the catheter. Optionally, the matrix may be stiffened to facilitate insertion into the catheter. Such stiffening may be achieved through choice of material for the matrix, by treating the material of the matrix, or other ways. In some embodiments, the matrix may be coated with a material to facilitate sliding engagement with the catheter.

Figure 2:
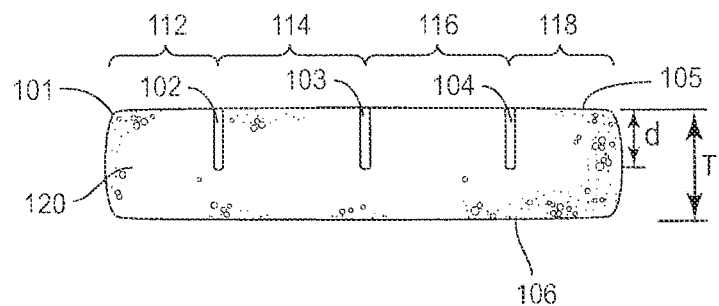
FIG. 2 provides a cross-sectional view of the implant body of FIG. 1 taken along line 2-2 and viewed in the direction of the arrows.
Figure 3:
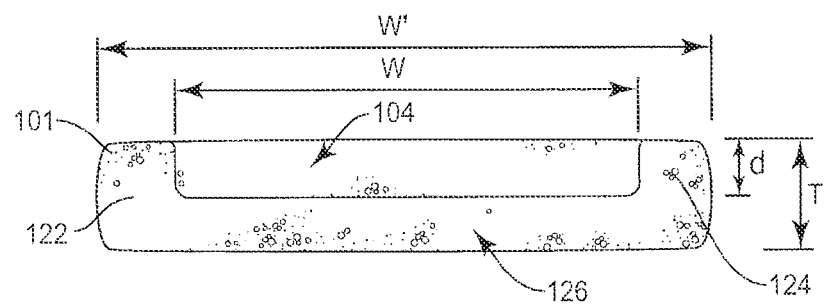
FIG. 3 provides a cross-sectional view of the implant body of FIG. 1 taken along line 3-3 and viewed in the direction of the arrows.

In the illustrative embodiment shown in FIGS. 1, 2 and 3, a medical device 100 having a matrix 101 is shown. This matrix can be, if desired, conformable to the target tissue site and broken into pieces.

Matrix 101 comprises a biocompatible implant material 120 and includes separation-assist lines in the form of three score lines 102, 103, and 104, rendering the medical device 100 separable into implant body pieces 112, 114, 116, 118. Matrix 101 includes an upper surface 105, a lower surface 106, and side walls 107, 108, 109 and 110. These can be burst release surfaces that immediately release the cell migration inhibitor composition. Alternatively, the cell migration inhibitor composition can be disposed in the core of the matrix that may contain entangled polymer to slow release of the cell migration inhibitor composition.

In the illustrated device having implant body 100, a rectangular configuration is provided. This may include for example an equilateral rectangle (square) configuration wherein walls 107-110 each have the same dimension, or a non-equilateral rectangle wherein walls 107 and 108 are of a lesser dimension than walls 109 and 110. Thus, overall matrix 100 includes a length L, defined as the dimension of walls 109 and 110 in a first direction, a width W defined by the dimension of walls 107 and 108 in a first direction, and a thickness T defined by the dimension of walls 107-110 in a second direction generally perpendicular to the first directions noted above.

In certain embodiments, the length L of the overall implant body 100 will range from about 1 cm to about 20 cm, the width W will range from about 1 cm to about 20 cm, and the thickness T will range from about 0.1 cm to about 3 cm. Length L may range from about 2 to about 5 cm, width W may range from about 2 to about 5 cm, and thickness T may range from about 0.3 to about 1 cm.

As to volume, advantageous implant bodies 100 can have a total volume of at least about 1 cubic centimeters (cc), e.g. in the range of about 1 cc to about 40 cc, and more typically in the range of about 2 cc to about 5 cc, although both smaller and larger overall volumes may also be used. Similarly, the volume of the pieces into which the implant bodies are configured to be separated may range from about 1 cc to about 40 cc, more typically in the range of about 2 cc to about 5 cc, although other piece volumes will also be suitable in broader aspects of the present principles.

In some embodiments, implant bodies 100 have a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ dynes/cm$^2$ to about $5 \times 10^5$ dynes/cm$^2$.

In some embodiments, the semi-solid or solid implant bodies 100 may comprise a polymer having a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the drug depot shown as a matrix may have a burst release surface that releases about 10%, 15%, 20%, 25%, 30%, 35%, 45%, to about 50% of the cell migration inhibitor composition over 24 or 48 hours.

With reference now particularly to FIGS. 2 and 3, provided in FIG. 2 is a cross-sectional view taken along line 2-2 of FIG. 1 and viewed in the direction of the arrows, and provided in FIG. 3 is a cross-sectional view taken along line 3-3 of FIG. 1 and viewed in the direction of the arrows. As shown, score lines 102, 103 and 104 extend from upper surface 105 of implant body 100 partially through the thickness T of the implant body 100. These score lines in the illustrated embodiment thus extend a depth d, which is thus less than the thickness T of the implant body 100. Depth d can be any suitable portion or percentage of thickness T, but depth d will generally represent 20% to 90% of thickness T, and depth d may represent about 30% to about 80% of thickness T. In certain forms, depth d may range from about 40% to about 60% of thickness T. In one embodiment, the implant bodies may be layered with varying thicknesses at every layer. In further embodiments, the implant bodies may be layered having a uniform thickness at every layer.

The score lines 102, 103 and 104 also extend only partially across the width W' of the implant body 100. In this manner, peripheral portions 122 and 124 will be provided at or near the periphery of implant body 100 and can serve to reinforce the overall integrity of implant body 100, for example relative to that integrity which would exist should score lines 102, 103 and 104 extend completely across the width W' of implant body 100. Thus, peripheral portions 122 and 124 are relatively thicker than portion 126 in the region in which the score line 104 extends. It will be understood that similar structures and features will exist for other score lines such as 102 and 103. The score lines can, in some embodiments, allow the matrix to be folded back upon itself and then implanted.

Matrix Delivery

It will be appreciated by those with skill in the art that the matrix (e.g., depot) can be administered to the target site using a "cannula" or "needle" that can be a part of a delivery device e.g., a syringe, a gun drug delivery device, or any medical device suitable for the application of a drug to a targeted organ or anatomic region. The cannula or needle of the device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the matrix implanted at this site for treating the condition. Typically, the transforaminal approach involves approaching the intervertebral space through the intervertebral foramina.

Some examples of lengths of the cannula or needle may include, but are not limited to, from about 15 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655 (mm). The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the matrix, the cannula or needle includes dose radiographic markers that indicate location at or near the site beneath the skin, so that the user may accurately position the matrix at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

In various embodiments, a method for delivering a matrix into a site of a patient is provided, the method comprising providing an implantable device comprising a porous matrix including a cell migration inhibitor composition (e.g., dextran), inserting a cannula at or near a target tissue site and implanting the matrix at the target site beneath the skin of the patient.

Advantageously, a matrix can be easily delivered to the target tissue site (e.g., abdomen, synovial joint, at or near the spinal column, etc.) and reduce, prevent or treat adhesion formation. In this way, accurate and precise implantation of the matrix in a minimally invasive procedure can be accomplished with minimal physical and psychological trauma to a patient.

In various embodiments, when the target site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

In one exemplary embodiment the depot is suitable for use in treating pain (e.g., neuropathic pain management) and/or to treat conditions (e.g., sciatica). The matrix may be inserted using a cannula or needle beneath the skin of a patient to a spinal site (e.g., spinal disc space, spinal canal, soft tissue surrounding the spine, nerve root, etc.) and one or more matrices are delivered to various sites along the spine. In this way, when several matrices are to be implanted, they are implanted in a manner that optimizes location, accurate spacing, and drug distribution.

Although the spinal site is discussed, as described above, the matrix can be delivered to any site beneath the skin, including, but not limited to, at least one muscle, ligament, tendon, cartilage, spinal disc, spinal foraminal space, near the spinal nerve root, or spinal canal.

In various embodiments, when the target tissue site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

"Localized" delivery includes delivery where one or more drugs are deposited within, at or near a tissue. For example, localized delivery includes delivery to a nerve root of the nervous system or a region of the brain, or in close proximity (within about 0.1 cm to 10 cm, for example) thereto. "Targeted delivery system" provides delivery of one or more drugs depots (e.g., gels or depot dispersed in the gel, etc.) having a quantity of therapeutic agent that can be deposited at or near the target tissue site as needed for prevention, reduction, or treatment of adhesions.

In some embodiments, one or more surfaces of the matrix comprise a barrier that can be made by cross-linking the matrix to prevent unwanted tissue growth. In addition, the dextran can act synergistically to prevent adhesion of scar tissue formation at or near the target tissue site where the matrix is placed. In some embodiments, the dextran is uniformly distributed throughout the matrix at a concentration of about 2-10% mg/ml concentration. In some embodiments, the dextran can be at discrete positions in or on a surface of the matrix. In some embodiments, the dextran can be disposed in the barrier portion of the matrix. In some embodiments, the dextran is disposed only in the non-barrier portion of the matrix.

Adhesions

Adhesions are abnormal, fibrous bands of scar tissue that can form inside the body as a result of the healing process that often follows open or minimally invasive surgical procedure including abdominal, gynecologic, cardiothoracic, spinal, plastic, vascular, ENT, ophthalmologic, urologic, neuro, or orthopedic surgery. Adhesions are typically connective tissue structures that form between adjacent injured areas within the body. Briefly, localized areas of injury trigger an inflammatory and healing response that culminates in healing and scar tissue formation. If scarring results in the formation of fibrous tissue bands or adherence of adjacent anatomical structures (that should normally be separate), adhesion formation is said to have occurred.

Adhesions can range from flimsy, easily separable structures to dense, tenacious fibrous structures that can only be separated by surgical dissection. Adhesion-related complications may include, for example, small bowel obstruction, infertility, chronic pelvic pain or back pain, and other complications. Adhesions from a previous procedure can also complicate a second surgery, whether the surgery is planned or unexpected. In addition, the abnormal orientation of tissues and organs caused by adhesions may lead to further discomfort and chronic pain.

"Reducing adhesions" refers to administering a composition so as to cause a reduction in the number of adhesions, extent of adhesions (e.g., area), and/or severity of adhesions (e.g., thickness or resistance to mechanical or chemical disruption) relative to the number, extent, and/or severity of adhesions that would occur without such administration. In various embodiments, reducing adhesions may be part of a protocol and also include performing a procedure (e.g., subsequent surgery to reduce adhesions). The composition or procedure may inhibit formation, or growth of adhesions following an adhesion promoting stimulus, may inhibit progression of adhesions, and/or may inhibit recurrence of adhesions following their spontaneous regression or following mechanical or chemical disruption.

"Preventing adhesions" refers to administering a therapeutic composition prior to formation of adhesions in order to reduce the likelihood that adhesions will form in response to a particular insult, stimulus, or condition. In various embodiments, preventing adhesions may be part of a protocol and also include performing a procedure (e.g., surgery to reduce adhesions). It will be appreciated that "preventing adhesions" does not require that the likelihood of adhesion formation is reduced to zero. Instead, "preventing adhesions" refers to a clinically significant reduction in the likelihood of adhesion formation following a particular insult or stimulus, e.g., a clinically significant reduction in the incidence or number of adhesions in response to a particular adhesion promoting insult, condition, or stimulus.

"Treating adhesions," refers to administering a composition that reverses, alleviates, reduces, and/or inhibits the progression and/or severity of adhesions, or reduces the likelihood of recurrence and/or the severity of recurrent adhesions. "Treating adhesions" also refers to administering or applying a composition that reverses, alleviates, reduces, inhibits the progression of, or reduces the likelihood of recurrence and/or severity of one or more symptoms of adhesions (e.g., pain, bowel obstruction, infertility, etc.). In various embodiments, treating adhesions may be part of a protocol and also include performing a procedure (e.g., surgery to reduce adhesions). Thus "treating adhesions" involves administering or applying a therapeutic composition and/or procedure once adhesion(s) have already formed following an insult or stimulus.

In various embodiments, the matrix can act as an adhesion barrier that can be administered or applied to the target tissue site before, during or after the surgery to reduce, prevent or treat adhesions. In some embodiments, the matrix, in addition to the dextran, creates a barrier that work by separating opposing tissue surfaces or tissue-organ surfaces while injured tissues heal. Ingrowth of scar tissue and the formation or reformation of adhesions immediately adjacent to the matrix is thus prevented.

The adhesion matrix could consist of a thin film or sponge composed of chemically modified sugars, in addition to the dextran, some of which occur naturally in the human body. The film or sponge adheres to tissues to which it is applied, and is slowly absorbed into the body over a period of about a week.

Another type of adhesion matrix is made of an amorphous bioresorbable copolymer, 70:30 poly(L-lactide-co-D, L-lactide), which is designed to match the natural lactic acid produced in the body. As an inert material, the body accepts the polymer and processes it through the normal channels of bulk hydrolysis, followed by further breakdown in the liver into $CO_2$ and $H_2O$, Still another type of adhesion matrix is based on PEG, which may be applied as two liquids, which are simultaneously sprayed onto the target area to form a soft adherent hydrogel. Within about one week, the hydrogel undergoes hydrolysis and is cleared from the body by the kidneys.

Sterilization

The matrix, and/or medical device to administer the matrix may be sterilizable. In various embodiments, one or more components of the matrix, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the matrix includes gelatin.

Other methods may also be used to sterilize the depot and/or one or more components of the device, including, but not limited to, gas sterilization, such as, for example, with ethylene oxide or steam sterilization.

In various embodiments, a kit is provided that may include additional parts along with the matrix and/or medical device combined together to be used to implant the matrix. The kit may include the matrix device in a first compartment. The second compartment may include a canister holding the matrix and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include an agent for radiographic imaging. Each tool may be separately packaged in a plastic pouch that is radiation sterilized. A cover of the kit may include illustrations of the implanting procedure and a clear plastic cover may be placed over the compartments to maintain sterility. In some embodiments, a kit is provided with instruction to use an injectable drug from another kit.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable device for reducing or preventing adhesion formation at a post-operative tissue site in a patient, the implantable device comprising a biodegradable porous polymer matrix comprising dextran sulfate, wherein the implantable device is configured to release the dextran sulfate over a period of at least 2 days, and the matrix is in a sponge form comprising poly(L-lactide-co-D, L-lactide) and having a density of between about 1.6 g/cm$^3$ and about 0.3 g/cm$^3$, and a core comprising dense entangled polymers of the implantable device does not contain dextran sulfate, and the matrix comprises an initial burst release surface disposed on edges of the matrix that releases 20% to 25% of dextran sulfate over 24 hours, and the average sulfur content of the dextran sulfate is 16% to 19%.

2. An implantable device according to claim 1, wherein the matrix is configured to release the dextran over at least 2 to 7 days.

3. An implantable device according to claim 1, wherein the matrix comprises a plurality of separation-assist lines defined in the sponge matrix, the separation-assist lines configured to facilitate separation of the sponge matrix into a plurality of pieces.

4. An implantable device according to claim 1, wherein the matrix is soaked, sprayed or impregnated with dextran sulfate.

5. An implantable device according to claim 1, wherein the dextran sulfate comprises (i) from about 5% to about 70% by weight based on a total weight of the implantable device; or (ii) from about 10% to about 50% by weight based on a total weight of the implantable device; or (iii) a concentration of about 1-30 mg/ml or about 2-10 mg/ml of the implantable device.

6. An implantable device according to claim 1, wherein the device releases: (i) a bolus dose of the dextran sulfate at a tissue site beneath the skin; and (ii) an effective amount of the dextran sulfate over a period of at least seven days.

7. An implantable device according to claim 1, wherein the matrix has a thickness of 0.4 mm to about 1 mm.

8. An implantable device according to claim 1, wherein the polymer comprises an inherent viscosity from about 0.10 dL/g to about 1.2 dL/g.

9. An implantable device according to claim 1, wherein the matrix comprises pores having a pore size from 250 to 500 microns.

10. An implantable device according to claim 1, wherein the poly(L-lactide-co-D, L-lactide) has a 70:30 ratio of L-lactide-co-D to L-lactide.

11. An implantable device according to claim 1, wherein the dextran sulfate has an average molecular weight of about 10,000 to about 60,000 Daltons.

12. An implantable device according to claim 1, wherein the implantable device is preservative free, and the implantable device comprises a concentration range of dextran sulfate between 20 mg/ml and 1 mg/ml.

13. An implantable device for reducing or preventing adhesion formation at a post-operative tissue site in a patient, the implantable device comprising a biodegradable porous polymer matrix comprising dextran sulfate, wherein the implantable device is configured for releasing the dextran sulfate over a period of at least 7 days, and the matrix is in a sponge form comprising poly(L-lactide-co-D, L-lactide) and having a density of between about 1.6 g/cm$^3$ and about 0.3 g/cm$^3$, and a core comprising dense entangled polymers of the implantable device does not contain dextran sulfate, and the matrix comprises an initial burst release surface disposed on edges of the matrix that releases 20% to 25% of dextran sulfate over 24 hours, and the average sulfur content of the dextran sulfate is 16% to 19%.

14. An implantable device according to claim 13, wherein the matrix further comprises collagen.

15. An implantable device according to claim 13, wherein the device releases: (i) a bolus dose of the dextran sulfate at a tissue site beneath the skin; and (ii) an amount of the dextran sulfate over a period of at least seven days.

* * * * *

UNITED STATES PATENT AND TRADEMARK OFFICE
CERTIFICATE OF CORRECTION

PATENT NO. : 9,707,323 B2
APPLICATION NO. : 13/674147
DATED : July 18, 2017
INVENTOR(S) : McKay Page 1 of 1

It is certified that error appears in the above-identified patent and that said Letters Patent is hereby corrected as shown below:

In the Specification

In Column 5, Line 65, delete "matrices)" and insert -- matrices)) --, therefor.

In Column 8, Line 63, delete "2-30 days;" and insert -- 2-30 days, --, therefor.

In Column 10, Lines 43-44, delete "type)(XVIII," and insert -- type XVIII, --, therefor.

In Column 11, Line 49, delete "non-harrier" and insert -- non-barrier --, therefor.

In Column 11, Lines 51-52, delete "in the matrix in the matrix" and insert -- in the matrix --, therefor.

In Column 11, Line 56, delete "about %" and insert -- about --, therefor.

In Column 18, Line 48, delete "$H_2O$," and insert -- $H_2O$. --, therefor.

Signed and Sealed this
Third Day of October, 2017

Joseph Matal
*Performing the Functions and Duties of the*
*Under Secretary of Commerce for Intellectual Property and*
*Director of the United States Patent and Trademark Office*